(12) United States Patent
Zhang et al.

(10) Patent No.: US 7,617,743 B2
(45) Date of Patent: Nov. 17, 2009

(54) DEVICE AND METHOD FOR DISTRIBUTING MEASUREMENT SAMPLE AND CLEANING TUBES

(75) Inventors: Yaohui Zhang, Shenzhen (CN); Cheng Zhang, Shenzhen (CN)

(73) Assignee: Shenzhen Mindray Bio-Medical Electronics Co., Ltd. (CN)

( * ) Notice: Subject to any disclaimer, the term of this patent is extended or adjusted under 35 U.S.C. 154(b) by 121 days.

(21) Appl. No.: 11/530,387

(22) Filed: Sep. 8, 2006

(65) Prior Publication Data

US 2008/0121051 A1    May 29, 2008

(30) Foreign Application Priority Data

May 17, 2006    (CN) .................. 2006 1 0035553

(51) Int. Cl.
*G01N 35/10* (2006.01)

(52) U.S. Cl. .................................... 73/864.22

(58) Field of Classification Search ............. 73/864.22; 422/63, 68.1
See application file for complete search history.

(56) References Cited

U.S. PATENT DOCUMENTS

| | | | | |
|---|---|---|---|---|
| 6,383,818 | B1 | 5/2002 | Arai et al. ................. | 436/177 |
| 6,689,615 | B1 | 2/2004 | Murto et al. ................ | 436/69 |
| 6,812,032 | B1 * | 11/2004 | Carver et al. ............... | 436/63 |
| 7,324,194 | B2 * | 1/2008 | Roche et al. ............... | 356/246 |
| 2003/0066347 | A1 | 4/2003 | Goloby | |
| 2007/0151984 | A1 * | 7/2007 | Baker et al. ............... | 222/129 |

FOREIGN PATENT DOCUMENTS

| | | |
|---|---|---|
| CN | 85 2 04477 U | 9/1986 |
| CN | 2563575 Y | 7/2003 |
| CN | 1437026 A | 8/2003 |
| FR | 2756628 | 6/1998 |
| JP | 2001264226 A * | 9/2001 |

OTHER PUBLICATIONS

SIPO Search Report for corresponding Chinese application, 4 pages, dated Jun. 1, 2006.
SIPO Office Action for corresponding Chinese application, 4 pages, dated May 30, 2008.
English translation of abstract for Chinese Patent Application No. 85204477 (reference above).
English translation of abstract for French Patent Application No. 2756628 (reference above).
SIPO Search Report for corresponding Chinese application, 4 pages, dated Jun. 1, 2006.
English translation of abstract for Chinese Patent Application No. 1437026A (reference above).
English translation of abstract for Chinese Patent Application No. 2563575Y(reference above).

* cited by examiner

*Primary Examiner*—Hezron Williams
*Assistant Examiner*—Tamiko D Bellamy
(74) *Attorney, Agent, or Firm*—Vista IP Law Group, LLP.

(57) ABSTRACT

Disclosed are a device and a method for distributing measurement sample and cleaning tubes. The device comprises a diluent container for accommodating a diluent therein; an aspirating tube for sucking a measurement sample; a first syringe for quantifying the measurement sample; a second syringe for quantifying the diluent; a first switching unit for switching between a first passage and a second passage; a bath; a sample buffer tube communicated with the first syringe; a dispensing tube for dispensing the measurement sample or the diluent into the bath; a second switching unit for switching between a third passage and a fourth passage. A reagent buffer tube, a reagent container and a third switching unit may be further provided between the sample buffer tube and the first syringe, or between the second switching unit and the input port of the dispensing tube.

11 Claims, 4 Drawing Sheets ns, and the third switching unit 3 is still in the constant-opened position, so that the second syringe 10, the first syringe 5 and a wipe block 19 are communicated to form a passage. At the same time, a pump 18 is turned on, a lift motor 17a is driven to raise the aspirating tube 12. And then, the power unit 4 is reversely driven so as to respectively push the pushing bars into barrels of the first syringe 5 and the second syringe 10. Consequently, the outer wall of the aspirating tube 12 is cleaned by the diluent sucked into the second syringe 10 and the wipe block 19 via the passage.

DEVICE AND METHOD FOR DISTRIBUTING MEASUREMENT SAMPLE AND CLEANING TUBES

CROSS-REFERENCE TO RELATED APPLICATION(S)

This application claims foreign priority under Title 35, United Stats Code, § 119(a)-(d) or § 365(b) to Chinese Patent Application No. 200610035553.6, which was filed on May 17, 2006 into the State Intellectual Property Office of the People's Republic of China.

FIELD OF THE INVENTION

The present invention relates to technology field of analysis on blood cells of human being or animal, and more particularly, relates to a device and a method for distributing measurement sample and cleaning tubes during analysis on blood cells.

BACKGROUND OF THE INVENTION

In medical field, blood cells of human being or animal will be measured and analyzed so as to determine disease or physical examination. For example, in the count of blood cells, a movable assembly of an aspirating probe is generally used in the current Hematology Analyzer. FIG. 1 is a schematic diagram illustrating the device for distributing measurement sample and cleaning tubes according to the current technology. As shown in FIG. 1, a first switching unit (such as solenoid valve) 1 has a normally open port NO, a normally closed port NC and a common port C. When the first switching unit 1 is switched off, the normally open port NO is communicated with the common port C, which is defined as a constant-opened position of the first switching unit 1. When the first switching unit 1 is switched on, the normally closed port NC is communicated with the common port C, which is defined as a constant-closed position of the first switching unit 1. Each of a second switching unit 2 and a third switching unit 3 can also have a constant-open position and a constant-closed position on a basis of the above same principle for the first switching unit 1. The first syringe 5 is used to quantify a measurement sample, so as to obtain red blood cell/platelet (RBC/PLT) count sample, while a second syringe 10 is used to quantify a Lyse, a diluent and the measurement sample, so as to obtain white blood cell/hemoglobin (WBC/HGB) count sample. The sampling and distributing a measurement sample is operated as follows.

1. Regarding the RBC/PLT Count Sample

The first switching unit 1, the second switching unit 2 and the third switching unit 3 are switched into the respective constant-opened positions, so that a second syringe 10 is communicated with the diluent container 11, while a first syringe 5, a Lyse buffer tube 14 and an aspirating tube 12 are communicated to form a passage. And then, a power unit (such as motor) 4 is driven to pull out a pushing bar of the first syringe 5, so that a measurement sample 7 is sucked from the test tube 6 and stored into the aspirating tube 12 via the passage. Since the first syringe 5 and the second syringe 10 are commonly driven by the power unit 4, pushing bars of the second syringe 10 and the first syringe 5 are synchronously pulled out by the power unit 4, so that a predetermined amount of the diluent is also sucked from a diluent container 11 into the second syringe 10.

Then, the first switching unit 1 and the second switching unit 2 are switched into the respective constant-closed posi- Next, the first switching unit 1 and the second switching unit 2 are switched into the respective constant-opened positions, and the third switching unit 3 is still in the constant-opened position, the pump 8 is turned off at the same time, so that the second syringe 10 is communicated with the diluent container 11. And then, the power unit 4 is driven so as to pull out the pushing bar of the second syringe 10. Consequently, the diluent is sucked from the diluent container 11 into the second syringe 10. When the diluent sucked into the second syringe 10 reaches a predetermined amount, the power unit 4 is stopped. Subsequently, a deflecting or horizontal motor 17b is driven to move the aspirating tube 12 above the bath 15, and then a lift motor 17a is driven to lower the aspirating tube 12.

Subsequently, the first switching unit 1 is switched into the constant-closed position, the second switching unit 2 and the third switching unit 3 are still in the respective constant-opened positions, so that the second syringe 10, the first syringe 5, the Lyse buffer tube 14 and the aspirating tube 12 are sequentially communicated to form a passage. And then, the power unit 4 is reversely driven so as to respectively push the pushing bars into the barrels of the first syringe 5 and the second syringe 10. Consequently, the measurement sample stored in the aspirating tube 12 and the diluent sucked into the second syringe TO are injected into the bath 15 via the passage.

2. Regarding the WBC/HGB Count Sample

The first switching unit 1 is switched into the constant-opened position, the second switching unit 2 and the third switching unit 3 are still in the respective constant-opened positions, so that the second syringe 10 is communicated with the diluent container 11, while the first syringe 5, the Lyse buffer tube 14, and the aspirating tube 12 are communicated to form a passage. And then, the deflecting or horizontal motor 17b is driven to wiggly move the aspirating tube 12 so as to homogeneously mix the measurement sample in the bath 15. Thereafter, the power unit 4 is driven so as to pull out the pushing bars of the first syringe 5 and the second syringe 10, and thus a desired amount of the measurement sample 7, which has been homogeneously mixed, is sucked from the bath 15 and stored into the aspirating tube 12 via the passage. At the same time, a predetermined amount of the diluent is sucked from the diluent container 11 into the second syringe 10.

Then, the first switching unit 1 and the second switching unit 2 are switched into the respective constant-closed positions, and the third switching unit 3 is still in the constant-opened position, so that the second syringe 10, the first syringe 5 and a wipe block 19 are communicated to form a passage. At the same time, the pump 18 is turned on, the lift motor 17a is driven to raise the aspirating tube 12. Thereafter, the power unit 4 is reversely driven so as to respectively push the pushing bars into the barrels of the first syringe 5 and the second syringe 10. Consequently, the outer wall of the aspirating tube 12 is cleaned by the diluent sucked into the second syringe 10 and the wipe block 19 via this passage.

Next, the first switching unit 1 and the second switching unit 2 are switched into the respective constant-opened positions, and the third switching unit 3 is still in the constant-opened position, so that the second syringe 10 is communicated with the diluent container 11; and at the same time, the pump 8 is turned off And then, the power unit 4 is driven so as to pull out the pushing bar of the second syringe 10. Consequently, the diluent is sucked from the diluent container 11 into the second syringe 10. When the diluent sucked into the second syringe 10 reaches a predetermined amount, the power unit 4 is stopped.

Subsequently, the first switching unit 1 is switched into the constant-closed position, the second switching unit 2 is still in the constant-opened position, and the third switching unit 3 is switched into the constant-closed position, so that the second syringe 10, the first syringe 5, the Lyse buffer tube 14 and the Lyse container 13 are communicated to form a passage. And then, the power unit 4 is driven so as to pull out the pushing bar of the second syringe 10. Consequently, a prescribed amount of the Lyse is sucked from the Lyse container 13 and stored into the Lyse buffer tube 14, and thereafter the power unit 4 is stopped.

And then, the first switching unit 1 is still in the constant-opened position, the second switching unit 2 is switched into the constant-opened position, and the third switching unit 3 is still in the constant-opened position, so that the second syringe 10, the first syringe 5, the Lyse buffer tube 14 and the aspirating tube 12 are communicated to form a passage. And then, the power unit 4 is reversely driven so as to respectively push the pushing bars into the barrels of the first syringe 5 and the second syringe 10. Consequently, the measurement sample stored in the aspirating tube 12, the diluent sucked into the second syringe 10, and the Lyse stored in the Lyse buffer tube 14 are injected into the bath 15 via the passage so as to obtain the WBC/HGB count sample. And thereafter, the power unit 4 is stopped.

With such Hematology Analyzer for collecting and distributing the measurement sample using the assembly of the aspirating tube, it is necessary to assure the movability and flexibility of the aspirating tube and assure that the aspirating tube can be cleaned, and thus the wipe block, the lift motor, and the deflecting or horizontal motor must be used. Consequently, the cost of such Hematology Analyzer is expensive, fluidic system and mechanical constructions are very complex, and it is difficult to design the arrangement of these constructions.

SUMMARY OF THE INVENTION

The technical problems to be resolved by the present invention is to provide a device and a method for distributing measurement sample and cleaning tubes, which has simple construction and effectively reduce the cost of manufacture.

According to an aspect of the present invention, a device for distributing measurement sample and cleaning tubes is provided. The device comprises: a diluent container for accommodating a diluent therein; an aspirating tube for sucking a measurement sample; a first syringe driven by a power unit and used to quantify the measurement sample; a second syringe driven by the power unit and used to quantify the diluent; a first switching unit connected to the first syringe, the second syringe and the diluent container, for switching between a communication of the second syringe with the diluent container and a communication of the second syringe with the first syringe; a bath; a sample buffer tube communicated with the first syringe at a port thereof; a dispensing tube for dispensing the measurement sample and/or the diluent into the bath; and a second switching unit connected to an output port of the aspirating tube, the other port of the sample buffer tube and an input port of the dispensing tube, for switching between a communication of the other port of the sample buffer tube with the input port of the dispensing tube and a communication of the other port of the sample buffer tube with the output port of the aspirating tube.

According to a first preferred embodiment of the device of the present invention, a reagent buffer tube, a reagent container for accommodating a reagent therein and a third switching unit may be further provided between the sample buffer tube and the first syringe, wherein the reagent buffer tube is communicated with the first syringe at a port thereof; the third switching unit is connected to the port of the sample buffer tube, the other port of the reagent buffer tube and the reagent container, for switching between a communication of the other port of the reagent buffer tube with the port of the sample buffer tube and a communication of the other port of the reagent buffer tube with the reagent container.

In the first preferred embodiment of the device of the present invention, the sample buffer tube may comprise a first sample buffer tube and a second sample buffer tube which are connected in series, the first sample buffer tube is connected to the second switching unit, the second sample buffer tube is connected to the third switching unit, and a length of the first sample buffer tube is shorter than that of the second sample buffer tube.

According to a second preferred embodiment of the device of the present invention, a reagent buffer tube, a reagent container for accommodating a reagent therein and a third switching unit may be further provided between the second switching unit and the input port of the dispensing tube, wherein the reagent buffer tube is communicated with the second switching unit at a port thereof; the third switching unit is connected to the input port of the dispensing tube, the other port of reagent buffer tube and the reagent container, for switching between a communication of the other port of the reagent buffer tube 14 with the input port of the dispensing tube and a communication of the other port of the reagent buffer tube with the reagent container.

In the second preferred embodiment of the device of the present invention, the sample buffer tube may comprise a first sample buffer tube and a second sample buffer tube which are connected in series, the first sample buffer tube is connected to the second switching unit, the second sample buffer tube is communicated with the first syringe, and a length of the first sample buffer tube is shorter than that of the second sample buffer tube.

In the preferred embodiments of the device of the present invention, the first switching unit, the second switching unit, and the third switching unit are preferably solenoid valves. In the preferred embodiments of the device of the present invention, preferably, a pushing bar of the first syringe and a pushing bar of the second syringe are synchronously moved by the power unit.

In the preferred embodiments of the device of the present invention, a capacity of the first syringe is smaller than that of the second syringe, and the capacity of the second syringe is larger than that of the aspirating tube.

According to an aspect of the present invention, a method for distributing measurement sample and cleaning tubes is provided. Said method comprises the steps of: step A: sucking a desired amount of a measurement sample through an aspirating tube so as to wash out a previous measurement sample remained in the aspirating tube and storing the measurement sample into a sample buffer tube which is communicated with the aspirating tube, sucking a diluent from a diluent container into a syringe, and then injecting the diluent which is sucked into the syringe and the measurement sample which is stored in the sample buffer tube into a bath via a dispensing tube communicated with the sample buffer tube so as to wash out the previous measurement sample remained in the sample buffer tube; and step B: sucking the measurement sample again through the aspirating tube and storing the measurement sample into the sample buffer tube, sucking a predetermined amount of the diluent again from the diluent container into the syringe, and injecting the diluent sucked into the syringe and the measurement sample stored in the sample buffer tube into the emptied bath via the dispensing tube so as to obtain a first count sample.

According to a preferred embodiment of said method of the present invention, said method further comprises the following steps after the step B: step C: sucking a diluent from a diluent container into a syringe, and then injecting the diluent which is sucked into the syringe into a bath via a dispensing tube communicated with the sample buffer tube so as to wash out the measurement sample remained in the sample buffer tube; and step D: sucking the measurement sample again through the aspirating tube and storing the measurement sample into the sample buffer tube, sucking the predetermined amount of the diluent again from the diluent container into the syringe, sucking an prescribed amount of a reagent from a reagent container and storing into a reagent buffer tube, and then injecting the diluent sucked into the syringe, the reagent stored in the reagent buffer tube, and the measurement sample stored in the sample buffer tube into the emptied bath via the dispensing tube so as to obtain a second count sample.

In the preferred embodiment of said method of the present invention, preferably, the sample buffer tube may comprise a first sample buffer tube and a second sample buffer tube which are connected in series, a length of the second sample buffer tube is shorter than that of the first sample buffer tube. More preferably, the measurement sample is sucked and stored into the first sample buffer tube in the step B; the measurement sample is and stored into the first sample buffer tube and the second sample buffer tube in the step D.

With the device for distributing measurement sample and cleaning tubes according to the present invention, the wipe block, the lift motor, the deflecting or horizontal motor in the prior art are omitted. The fluidic system and mechanical construction are simplified, and thus the cost of manufacture is reduced, the control complexity is lowered.

BRIEF DESCRIPTION OF DRAWINGS

The above objects, aspects, features and advantages will be apparent from the following description in combination with the drawings, in which.

DETAILED DESCRIPTION OF THE PREFERRED EMBODIMENTS

Hereinafter, a method and a device for distributing measurement sample and cleaning tubes according to the present invention during analysis on cells of blood will be described.

For the sake of simplification, a device for distributing measurement sample and cleaning tubes and a method using the same according to the present invention will be described herein with respect to the preparation of RBC/PLT and WBC/HGB count samples of blood sample, but the present invention is not limited by these embodiments. The device and the method of the present invention can be applied into the preparation of other cell count samples of blood sample. For example, the corresponding reagent can be used to replace a Lyse which is used to obtain WBC/HGB count sample.

Figure 1:
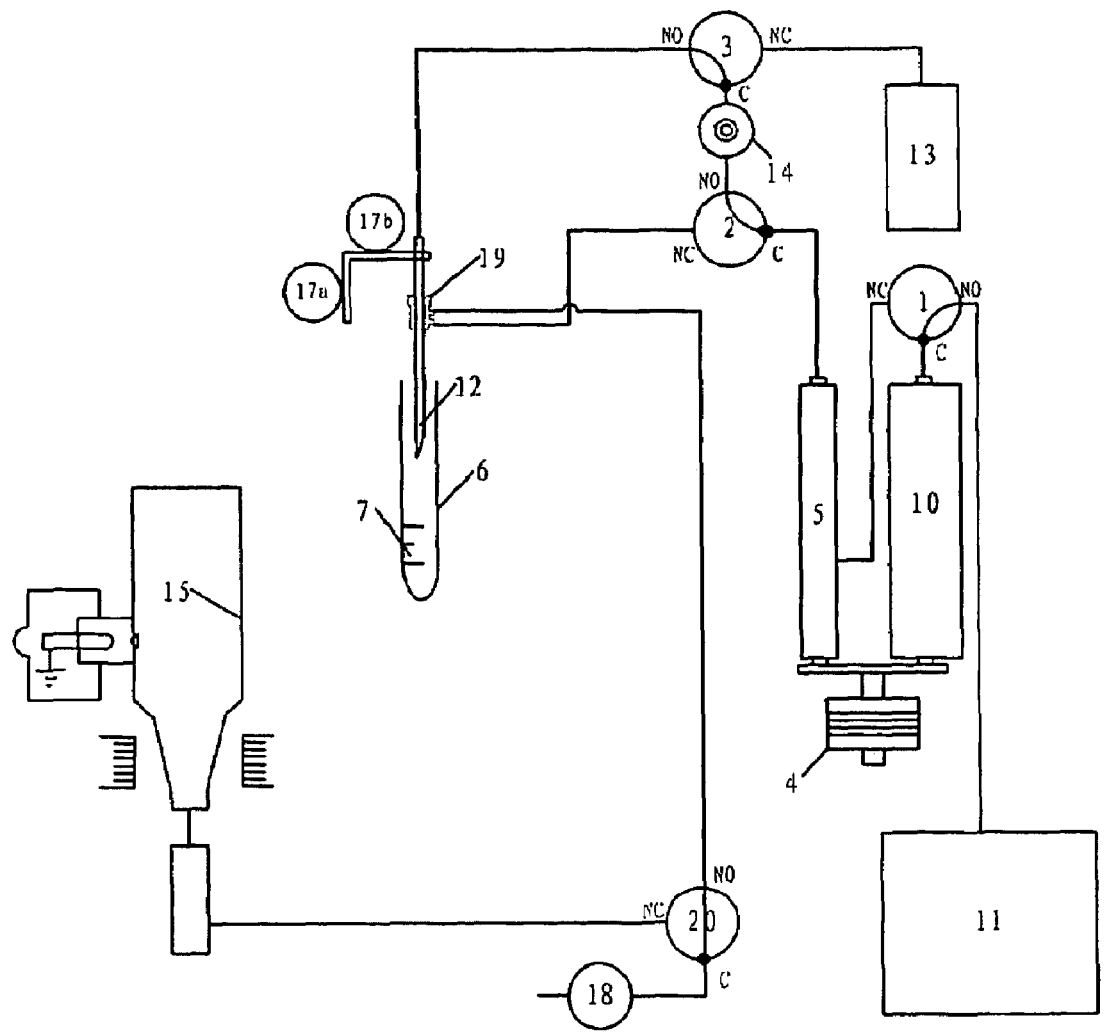
FIG. 1 is a schematic diagram illustrating a device for distributing measurement sample and cleaning tubes according to the prior art.
Figure 2:
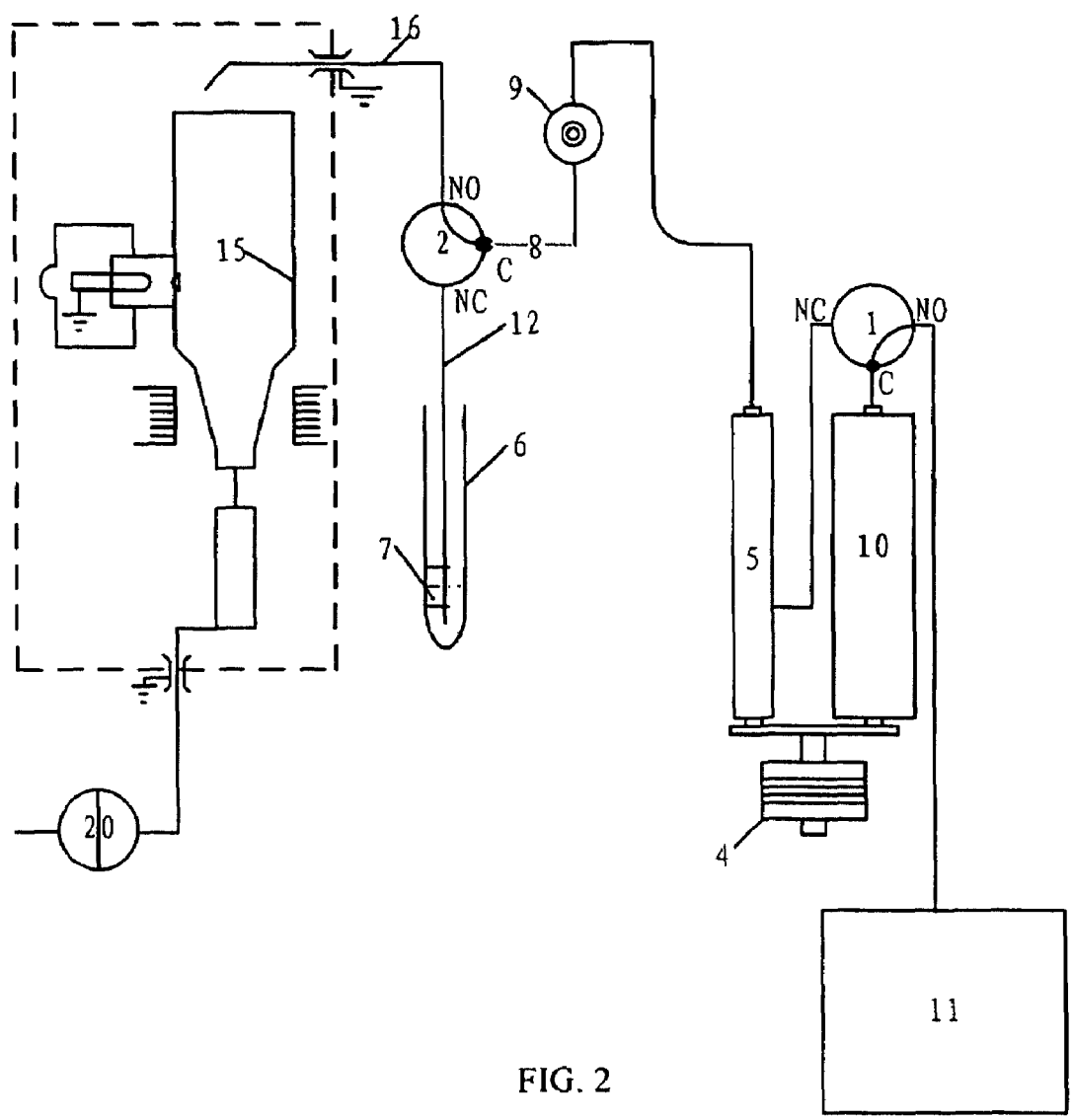
FIG. 2 is a schematic diagram illustrating a basis construction of a device for distributing measurement sample and cleaning tubes according to the present invention.
Figure 3:
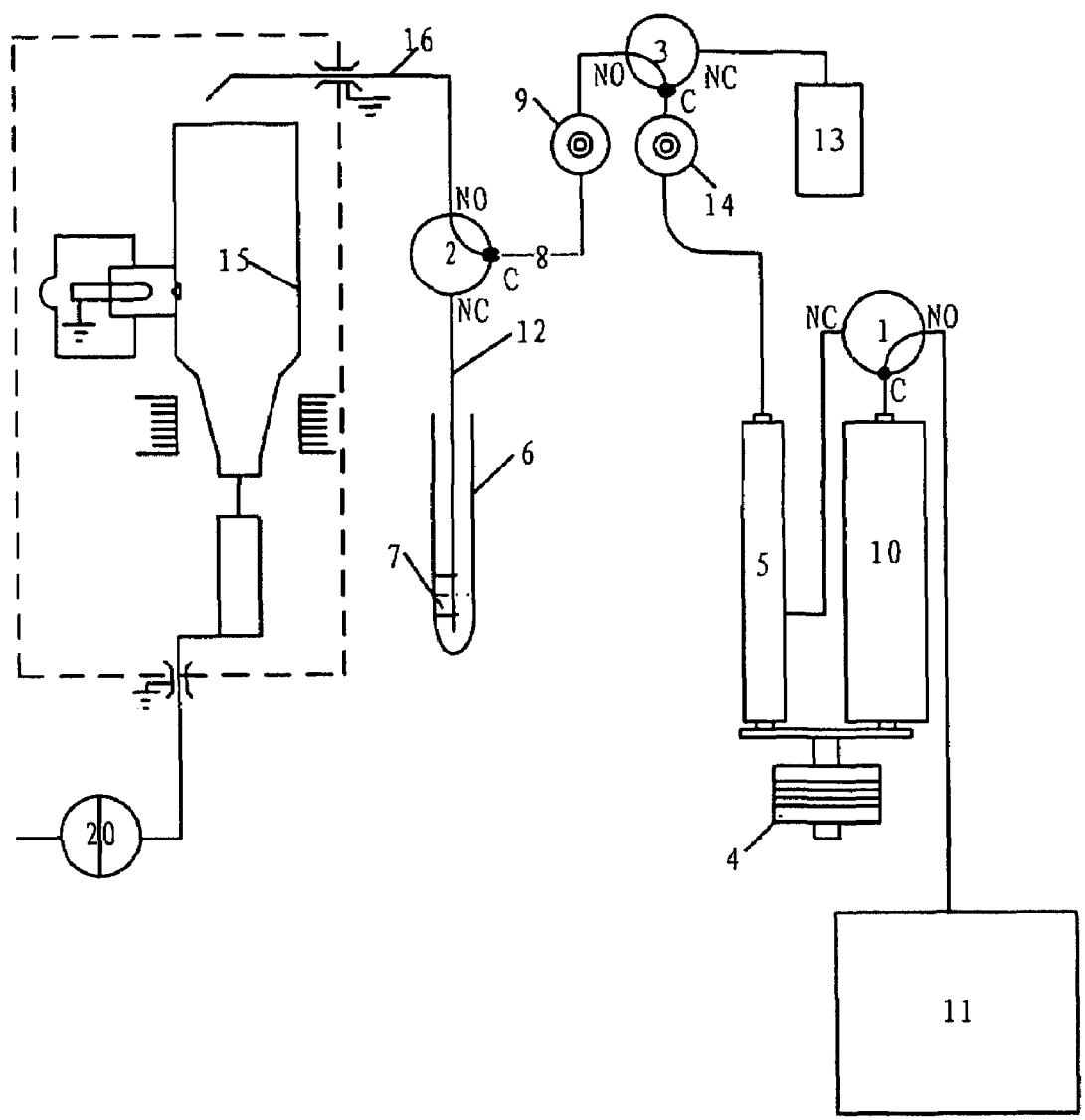
FIG. 3 is a schematic diagram illustrating a device for distributing measurement sample and cleaning tubes according to a first embodiment of the present invention.
Figure 4:
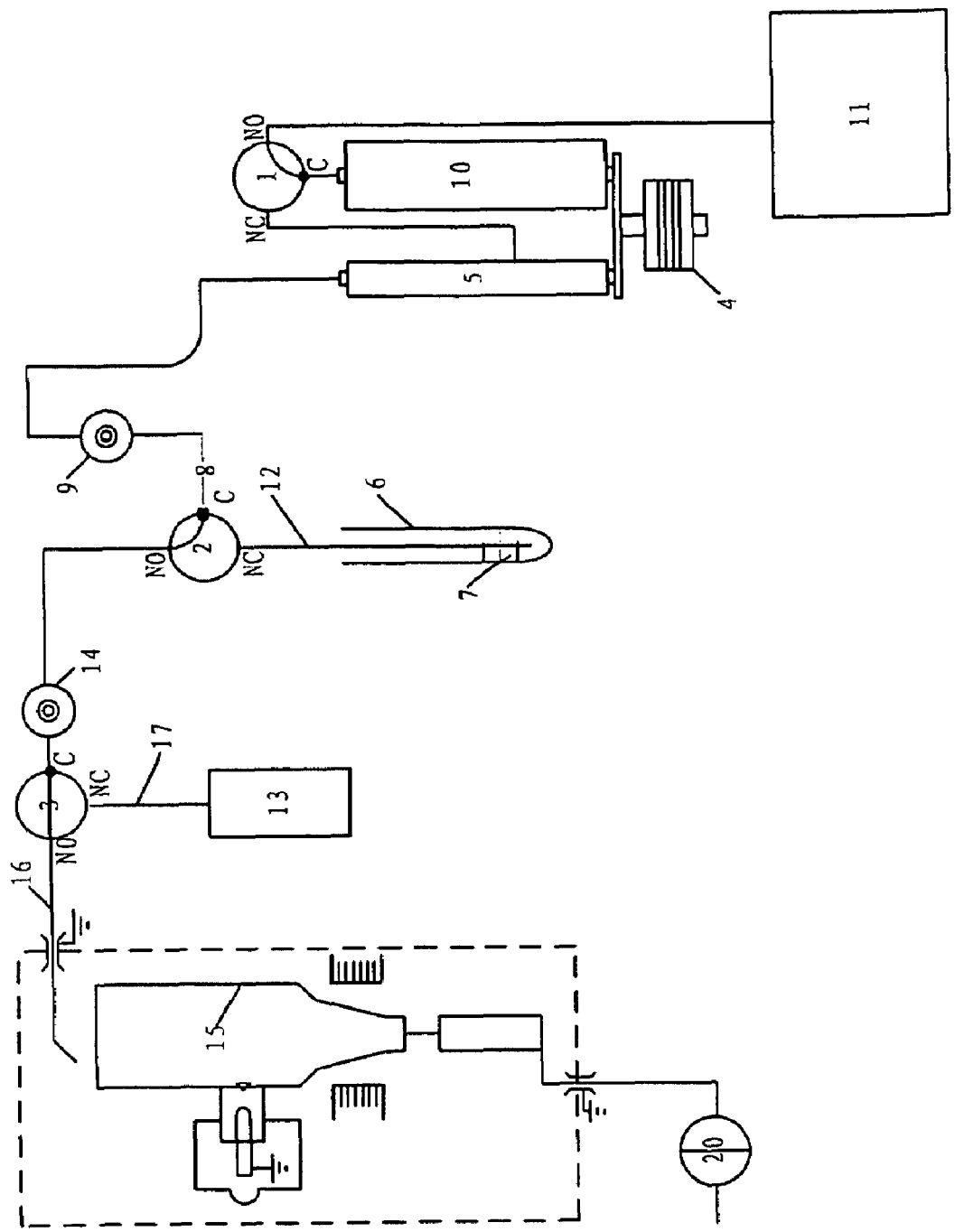
FIG. 4 is a schematic diagram illustrating a device for distributing measurement sample and cleaning tubes according to a second embodiment of the present invention.

Hereinafter, the embodiments of the present invention will be described with reference to the drawings. FIG. 2 is a schematic diagram illustrating a basis construction of a device for distributing measurement sample and cleaning tubes according to the present invention, FIG. 3 is a schematic diagram illustrating a device for distributing measurement sample and cleaning tubes according to a first embodiment of the present invention, and FIG. 4 is a schematic diagram illustrating a device for distributing measurement sample and cleaning tubes according to a second embodiment of the present invention. The elements in the present invention with the same function as that in the prior art are given with the same reference signs.

As shown in FIG. 2, a basis construction of a device for distributing measurement sample and cleaning tubes according to the present invention comprises: a diluent container 11 for accommodating a diluent therein; an aspirating tube 12 for sucking measurement sample 7; a first syringe 5 driven by a power unit 4 and used to quantify the measurement sample 7; a second syringe 10 driven by the power unit 4 and used to quantify the diluent; a first switching unit 1 having a normally closed port NC, a common port C and a normally open port NO which are respectively connected to the first syringe 5, the second syringe 10 and the diluent container 11, and switching so as to selectively communicate the second syringe 10 with the diluent container 11 or the first syringe 5; a bath 15; a sample buffer tube (described hereinafter) communicated with the first syringe 5 at a port thereof, a dispensing tube 16 for dispensing the measurement sample and/or the diluent into the bath 15; a second switching unit 2 having a normally closed port NC, a common port C and a normally open port NO which are respectively connected to an output port of the aspirating tube 12, the other port of the sample buffer tube and an input port of the dispensing tube 16, and switching so as selectively to communicate the other port of the sample buffer tube with the input port of the dispensing tube 16 or the output port of the aspirating tube 12.

As shown in FIGS. 3 and 4, a Lyse buffer tube 14, a third switching unit 3 and a Lyse container 13 can be further provided at different positions of the above basis construction, so as to construct devices for distributing measurement sample and cleaning tubes according to a first embodiment and a second embodiment of the present invention, respectively.

As shown in FIG. 3, on a basis of the above construction, a device for distributing measurement sample and cleaning tubes according to the first embodiment of the present invention is constructed as follows. A Lyse buffer tube 14, a Lyse container 13 for accommodating Lyse therein and a third switching unit 3 may be further provided between the sample buffer tube and the first syringe 5, wherein the Lyse buffer tube 14 is communicated with the first syringe 5 at a port thereof; the third switching unit 3 has a normally closed port NC, a common port C and a normally open port NO which are respectively connected to the port of the sample buffer tube, the other port of the Lyse buffer tube 14 and the Lyse container 13. The third switching unit 3 is capable of selectively switching into the constant-opened position so as to communicate the other port of the Lyse buffer tube 14 with the port of the sample buffer tube and thus realize the communication between the port of the sample buffer tube and the first syringe 5, or switching into the constant-closed position so as to communicate the other port of the Lyse buffer tube 14 with the Lyse container 13.

As shown in FIG. A, on a basis of the above construction, a device for distributing measurement sample and cleaning tubes according to a second embodiment of the present invention is constructed as follows. The Lyse buffer tube 14, the Lyse container 13 for accommodating Lyse therein and the third switching unit 3 may be further provided between the second switching unit 2 and the input port of the dispensing tube 16, wherein the Lyse buffer tube 14 is communicated with the second switching unit 2 at a port thereof; the third switching unit 3 has a normally closed port NC, a common port C and a normally open port NO which are respectively connected to the input port of the dispensing tube 16, the other port of Lyse buffer tube 14 and the Lyse container 13. The third switching unit 3 is capable of selectively switching into the constant-opened position so as to communicate the other port of the Lyse buffer tube 14 with the input port of the dispensing tube 16, and cooperates with the second switching unit 2 (i.e. the second switching unit 2 is also in the constant-opened position) so as to communicate the other port of the sample buffer tube with the input port of the dispensing tube 16; or switching into the constant-closed position so as to communicate the other port of the Lyse buffer tube 14 with the Lyse container 13.

In all the above embodiments, the first switching unit 1, the second switching unit 2 and the third switching unit 3 are preferably solenoid valves. The communication among the different ports of each switching unit is the same as that in the prior art.

In the first embodiment, the sample buffer tube may comprise a first sample buffer tube 8 and a second sample buffer tube 9 which are connected in series, wherein the first sample buffer tube 8 is connected to the second switching unit 2, the second sample buffer tube 9 is connected to the third switching unit 3, and a length of the first sample buffer tube 8 is shorter than that of the second sample buffer tube 9.

In the second embodiment, the sample buffer tube may comprise a first sample buffer tube 8 and a second sample buffer tube 9 which are connected in series, wherein the first sample buffer tube 8 is connected to the second switching unit 2, the second sample buffer tube 9 is communicated with the first syringe 5, and a length of the first sample buffer tube 8 is shorter than that of the second sample buffer tube 9.

The material used to form the first sample buffer tube 8 is such that the inner wall of the first sample buffer tube 8 is smooth enough so as to be adhered with little or none measurement sample.

In all the above embodiments, a pushing bar of the first syringe 5 and a pushing bar of the second syringe 10 are synchronously moved by the power unit 4, or a barrel of the first syringe 5 and a barrel of the second syringe 10 are synchronously moved by the power unit 4. A capacity of the first syringe 5 is smaller than that of the second syringe 10, and the capacity of the second syringe 10 is larger than that of the aspirating tube 12.

In all the above embodiments, the power unit 4 is preferably a motor.

In all the above embodiments, the measurement sample 7 may be stored into a test tube 6 in advance.

In all the above embodiments, a two-way solenoid valve 20 is provided below the bath 15.

Hereinafter, the operation of the device for distributing measurement sample and cleaning tubes according to a first embodiment of the present invention will be described in details with reference to FIG. 3.

First step, cleaning the sample buffer tube and the aspirating tube before preparing the RBC/PLT count sample:

(1) sucking the measurement sample from the test tube through the aspirating tube so as to wash out a previous measurement sample remained in the aspirating tube:

The first switching unit 1 and the second switching unit 2 are switched into the respective constant-closed positions, the second switching unit 3 is in the constant-opened position, so that the second syringe 10, the first syringe 5, the Lyse buffer tube 14, the second sample buffer tube 9, the first sample buffer tube 8 and the aspirating tube 12 are sequentially communicated to form a passage. And then, the power unit 4 is driven so as to pull out the pushing bar of the first syringe 5 and the pushing bar of the second syringe 10, and thus the measurement sample 7 is sucked from the test tube 6 via the passage, for washing out a previous measurement sample which is remained in the aspirating tube 12 during the previous operation. In order to ensure that the sucked measurement sample 7 this time is enough to wash out the previous measurement sample which is remained in the aspirating tube 12 during the previous operation, an amount sucked by the second syringe 10 at this time is preferably larger than the capacity of the aspirating tube 12, so that all the capacity of the aspirating tube 12 will be occupied by the sucked measurement sample 7, and the previous measurement sample which is remained in the aspirating tube 12 during the previous operation will be completely stored into the sample buffer tube. And then, the power unit 4 is stopped.

(2) sucking a desired amount of the diluent from the diluent container into the second syringe:

The first switching unit 1 and the second switching unit 2 are switched into the respective constant-opened positions, and the third switching unit 3 is still in the constant-opened position, so that the second syringe 10 is communicated with the diluent container 11, while the first syringe 5, the Lyse buffer tube 14, the second sample buffer tube 9, the first sample buffer tube 8 and the dispensing tube 16 are sequentially communicated to form a passage. And then, the power unit 4 is continuously driven so as to continue to pull out the pushing bars of the first syringe 5 and the second syringe 10, and thus the diluent is sucked from the diluent container 11 into the second syringe 10. When the amount of the diluent sucked into the second syringe 10 reaches the predetermined amount, the power unit 4 is stopped.

(3) washing out the previous measurement sample stored in the sample buffer tube by using the diluent:

The first switching unit 1 is switched into the constant-closed position, the second switching unit 2 and the third switching unit 3 are still in the respective constant-opened positions, so that the second syringe 10, the first syringe 5, the Lyse buffer tube 14, the second sample buffer tube 9, the first sample buffer tube 8 and the dispensing tube 16 are sequentially communicated to form a passage. And then, the power unit 4 is reversely driven so as to respectively push the pushing bars into the barrels of the first syringe 5 and the second syringe 10, thus the diluent sucked into the second syringe 10 washes and moves the previous measurement sample which is just stored in the sample buffer tube into the bath 15.

If necessary, the substeps (1), (2) and (3) of the first step can be repeated several times, or only the substeps (2) and (3) of the first step can be repeated several times, so as to repeatedly clean the previous measurement sample remained in the sample buffer tube by the diluent sucked into the second syringe 10, until the amount of the previous measurement sample residing in the sample buffer tube meets the desired requirement.

Second step: preparing the measurement sample with a special dilution ratio so as to obtain the RBC/PLT count sample:

(1) sucking the measurement sample and storing it into the sample buffer tube, while sucking the diluent into the second syringe:

After cleaning the sample buffer tube and the aspirating tube 12, the first switching unit 1 is switched into the constant-opened position, the second switching unit 2 is switched into the constant-closed position, the third switching unit 3 is still in the constant-opened position, so that the second syringe 10 is communicated with the diluent container 11, while the first syringe 5, the Lyse buffer tube 14, the second sample buffer tube 9, the first sample buffer tube 8 and the aspirating tube 12 are sequentially communicated to form a passage. And then, the power unit 4 is driven so as to pull out the pushing bars of the first syringe 5 and the second syringe 10, and thus the measurement sample in the test tube 6 is sucked and stored into the sample buffer tube via the passage. At the same time, the diluent is sucked from the diluent container 11 into the second syringe 10. When the measurement sample stored in the sample buffer tube reaches the desired amount, the power unit 4 is stopped.

(2) obtaining the measurement sample with a special dilution ratio (i.e. the RBC/PLT count sample) by using the measurement sample stored in the sample buffer tube and the diluent sucked into the second syringe:

The first switching unit 1 is still in the constant-opened position, the second switching unit 2 is switched into the constant-opened position, and the third switching unit 3 is still in the constant-opened position, so that the second syringe 10 is still communicated with the diluent container 11, while the first syringe 5, the Lyse buffer tube 14, the second sample buffer tube 9, the first sample buffer tube 8 and the dispensing tube 16 are sequentially communicated to form a passage. And then, the power unit 4 is driven so as to continuous to pull out the pushing bars of the first syringe 5 and the second syringe 10, and thus the diluent is continuously sucked from the diluent container 11 into the second syringe 10. When the total amount of the diluent sucked into the second syringe 10 reaches a predetermined amount, the power unit 4 is stopped. It should be noted that the first sample buffer tube 8 preferably has enough length so as to prevent the measurement sample 7 stored in the sample buffer tube from entering into the second sample buffer tube 9 via this passage. Thus the measurement sample will be completely stored in the first sample buffer tube 8.

And then, the first switching unit 1 is switched into the constant-closed position, the second switching unit 2 and the third switching unit 3 are still in the respective constant-opened positions, so that the second syringe 10, the first syringe 5, the Lyse buffer tube 14, the second sample buffer tube 9, the first sample buffer tube 8 and the dispensing tube 16 are sequentially communicated to form a passage. And then, the power unit 4 is reversely driven so as to respectively push the pushing bars into the barrels of the first syringe 5 and the second syringe 10. And thus, the desired amount of the measurement sample stored in the sample buffer tube and a predetermined amount of the diluent sucked into the second syringe 10 are injected into the bath 15 via the passage.

Consequently, the measurement sample with a special dilution ratio, i.e. the RBC/PLT count sample, is obtained. Finally, the power unit 4 is stopped.

Third step: cleaning the sample buffer tube and the Lyse buffer tube after the preparation of the RBC/PLT counting sample is completed:

The same procedures of substeps (2) and (3) of the step 1 can be performed in the third step, therefore the detail description for the third step is omitted here. After the sample buffer tube and the Lyse buffer tube 14 are cleaned, the power unit 4 is stopped.

Fourth step: preparing the measurement sample which is mixed with the Lyse and has a special dilution ratio, so as to obtain the WBC/HGB count sample:

(1) sucking a desired amount of the measurement sample and storing it into the sample buffer tube:

The first switching unit 1 and the second switching unit 2 are switched into the respective constant-closed positions, the third switching unit 3 is switched into the constant-opened position, so that the second syringe 10, the first syringe 5, the Lyse buffer tube 14, the second sample buffer tube 9, the first sample buffer tube 8 and the aspirating tube 12 are sequentially communicated to form a passage. And then, the power unit 4 is driven so as to pull out the pushing bars of the first syringe 5 and the second syringe 10, and thus the measurement sample in the test tube 6 is sucked and stored into the sample buffer tube via the passage. When the measurement sample stored in the sample buffer tube reaches the desired amount, the power unit 4 is stopped. At this time, the measurement sample is stored into the first sample buffer tube 8 and the second sample buffer tube 9.

(2) sucking a predetermined amount of the diluent into the second syringe:

The first switching unit 1 and the second switching unit 2 are switched into the respective constant-opened positions, the third switching unit 3 is still in the constant-opened position, so that the second syringe 10 is communicated with the diluent container 11, while the first syringe 5, the Lyse buffer tube 14, the second sample buffer tube 9, the first sample buffer tube 8 and the dispensing tube 16 are sequentially communicated to form a passage. And then, the power unit 4 is driven so as to continuous to pull out the pushing bar of the first syringe 5 and the pushing bar of the second syringe 10, and thus the diluent is sucked from the diluent container 11 into the second syringe 10. When the diluent sucked into the second syringe 10 reaches a predetermined amount, the power unit 4 is stopped. It should be noted that the second sample buffer tube 9 preferably has enough length so as to prevent the measurement sample 7 stored in the sample buffer tube from entering the first syringe 5 via this passage.

(3) sucking an prescribed amount of the Lyse and storing it into the Lyse buffer tube:

The first switching unit 1 is switched into the constant-closed position, the second switching unit 2 is still in the constant-opened position, and the third switching unit 3 is switched into the constant-closed position, so that the second syringe 10, the first syringe 5, the Lyse buffer tube 14 and the Lyse container 13 are sequentially communicated to form one passage, but the second sample buffer tube 9, the first sample buffer tube 8 and the dispensing tube 16 are sequentially communicated to form another passage, the two passages are not communicated. And then, the power unit 4 is driven so as to continuous to pull out the pushing bars of the first syringe 5 and of the second syringe 10, and thus the Lyse is sucked from the Lyse container 13 and stored into the Lyse buffer tube 14 via the one passage. When the Lyse stored in the Lyse buffer tube 14 reaches a prescribed amount, the power unit 4 is stopped.

(4) preparing the measurement sample which is mixed with the Lyse and has a special dilution ratio, and thus obtaining the WBC/HGB count sample:

The first switching unit 1 is switched into the constant-closed position, the second switching unit 2 is still in constant-opened position, and the third switching unit 3 is switched into the constant-opened position, so that the second syringe 10, the first syringe 5, the Lyse buffer tube 14, the second sample buffer tube 9, the first sample buffer tube 8 and the dispensing tube 16 are sequentially communicated to form a passage. And then, the power unit 4 is reversely driven so as to respectively push the pushing bars into the barrels of the first syringe 5 and the second syringe 10. And thus, the desired amount of the measurement sample stored in the sample buffer tube, the prescribed amount of the Lyse stored in the Lyse buffer tube 14, and a predetermined amount of the diluent sucked into the second syringe 10 are injected into the bath 15 via the passage. Consequently, the measurement sample which is mixed with the Lyse and has a special dilution ratio is obtained, and thus the WBC/HGB count sample is obtained. Finally, the power unit 4 is stopped.

Fifth step, cleaning tubes after preparation the WBC/HGB count sample:

(1) The first switching unit 1 is switched into the constant-opened position, the second switching unit 2 and the third switching unit 3 are still in the respective constant-opened positions, so that the second syringe 10 is communicated with the diluent container 11. And then, the power unit 4 is driven so as to respectively pull out the pushing bars from the barrels of the first syringe 5 and the second syringe 10, and thus the diluent is sucked from the diluent container 11 into the second syringe 10. When the diluent sucked into the second syringe 10 reaches a predetermined amount, the power unit 4 is stopped.

(2) Then, the first switching unit 1 is switched into the constant-closed position, the second switching unit 2 and the third switching unit 3 are still in the respective constant-opened positions, so that the second syringe 10 is not communicated with the diluent container 11, but the second syringe 10, the first syringe 5, the Lyse buffer tube 14, the second sample buffer tube 9, the first sample buffer tube 8 and the dispensing tube 16 are sequentially communicated to form a passage. And then, the power unit 4 is reversely driven so as to respectively push the pushing bars into the barrels of the first syringe 5 and the second syringe 10. And thus, the predetermined amount of the diluent sucked into the second syringe 10 is injected into the bath 15 via the passage, and washes out the measurement sample remained in the sample buffer tube and the dispensing tube 16, and the Lyse remained in the Lyse buffer tube 14, the second sample buffer tube 9, the first sample buffer tube 8 and the dispensing tube 16.

If necessary, the substeps (1) and (2) of the fifth step can be repeated several times so as to clean the Lyse buffer tube 14, the second sample buffer tube 9, the first sample buffer tube 8 and the dispensing tube 16, until the amount of the measurement sample of WBC/HGB and the Lyse which is remained in these pipes meets the desired requirement.

It should be noted that the fifth step during the above operation can be omitted. That is to say, the first step will be used to clean tubes during the repetition of the first step to the fourth step, therefore an additional step for cleaning tubes will not be required.

Hereinafter, the operation of the device for distributing measurement sample and cleaning tubes according to the second embodiment of the present invention will be described in details with reference to FIG. 4. Since the Lyse container 13, the Lyse buffer tube 14 and the third switching unit 3 are provided at a position which is different from the case of the first embodiment of the present invention, the operation of the device for distributing measurement sample and cleaning tubes according to the second embodiment of the present invention is different from the operation of the device for distributing measurement sample and cleaning tubes according to the first embodiment of the present invention.

The operation of the device for distributing measurement sample and cleaning tubes according to the second embodiment of the present invention will be described in details as follows.

First step, cleaning the sample buffer tube and the aspirating tube before preparing the RBC/PLT count sample:

(1) sucking the measurement sample from the test tube through the aspirating tube so as to wash out a previous measurement sample remained in the aspirating tube:

The first switching unit 1 and the second switching unit 2 are switched into the respective constant-closed positions, the second switching unit 3 is in the constant-opened position, so that the second syringe 10, the first syringe 5, the second sample buffer tube 9, the first sample buffer tube 8 and the aspirating tube 12 are sequentially communicated to form a passage. And then, the power unit 4 is driven so as to pull out the pushing bar of the first syringe 5 and the pushing bar of the second syringe 10, and thus the measurement sample 7 is sucked from the test tube 6 via the passage, for washing out a previous measurement sample which is remained in the aspirating tube 12 during the previous operation. In order to ensure that the sucked measurement sample 7 this time is enough to wash out the previous measurement sample which is remained in the aspirating tube 12 during the previous operation, an amount of the capacity sucked by the second syringe 10 is preferably larger than the capacity of the aspirating tube 12, so that all the capacity of the aspirating tube 12 will be occupied by the sucked measurement sample 7, and the previous measurement sample which is remained in the aspirating tube 12 during the previous operation will be completely stored into the sample buffer tube. And then, the power unit 4 is stopped.

(2) sucking a desired amount of the diluent from the diluent container into the second syringe:

The first switching unit 1 and the second switching unit 2 are switched into the respective constant-opened positions, and the third switching unit 3 is still in the constant-opened position, so that the second syringe 10 is communicated with the diluent container 11, while the first syringe 5, the second sample buffer tube 9, the first sample buffer tube 8, the Lyse buffer tube 14 and the dispensing tube 16 are sequentially communicated to form a passage. And then, the power unit 4 is continuously driven so as to continue to pull out the pushing bars of the first syringe 5 and the second syringe 10, and thus the diluent is sucked from the diluent container 11 into the second syringe 10. When the amount of the diluent sucked into the second syringe 10 reaches the predetermined amount, the power unit 4 is stopped.

(3) washing out the previous measurement sample stored in the sample buffer tube by using the diluent:

The first switching unit 1 is switched into the constant-closed position, the second switching unit 2 and the third switching unit 3 are still in the respective constant-opened positions, so that the second syringe 10, the first syringe 5, the second sample buffer tube 9, the first sample buffer tube 8, the Lyse buffer tube 14 and the dispensing tube 16 are sequentially communicated to form a passage. And then, the power unit 4 is reversely driven so as to respectively push the pushing bars into the barrels of the first syringe 5 and the second syringe 10, thus the diluent sucked into the second syringe 10 washes and moves the previous measurement sample which is just stored in the sample buffer tube into the bath 15.

If necessary, the substeps (1), (2) and (3) of the first step can be repeated several times, or only the substeps (2) and (3) of the first step can be repeated several times, so as to repeatedly clean the previous measurement sample residing in the sample buffer tube by the diluent sucked into the second syringe 10, until the amount of the previous measurement sample residing in the sample buffer tube meets the desired requirement.

Second step: preparing the measurement sample with a special dilution ratio so as to obtain the RBC/PLT count sample:

(1) sucking the measurement sample and storing it into the sample buffer tube, while sucking the diluent into the second syringe:

After cleaning the sample buffer tube and the aspirating tube 12, the first switching unit 1 is switched into the constant-opened position, the second switching unit 2 is switched into the constant-closed position, the third switching unit 3 is still in the constant-opened position, so that the second syringe 10 is communicated with the diluent container 11, while the first syringe 5, the second sample buffer tube 9, the first sample buffer tube 8, the Lyse buffer tube 14 and the aspirating tube 12 are sequentially communicated to form a passage. And then, the power unit 4 is driven so as to pull out the pushing bars of the first syringe 5 and the second syringe 10, and thus the measurement sample in the test tube 6 is sucked and stored into the sample buffer tube via the passage. At the same time, the diluent is sucked from the diluent container 11 into the second syringe 10. When the measurement sample stored in the sample buffer tube reaches the desired amount, the power unit 4 is stopped.

(2) obtaining the measurement sample with a special dilution ratio (i.e. the RBC/PLT count sample) by using the measurement sample stored in the sample buffer tube and the diluent sucked into the second syringe:

The first switching unit 1 is still in the constant-opened position, the second switching unit 2 is switched into the constant-opened position, and the third switching unit 3 is still in the constant-opened position, so that the second syringe 10 is still communicated with the diluent container 1T, while the first syringe 5, the second sample buffer tube 9, the first sample buffer tube 8, the Lyse buffer tube 14 and the dispensing tube 16 are sequentially communicated to form a passage. And then, the power unit 4 is driven so as to continuous to pull out the pushing bar of the first syringe 5 and the pushing bar of the second syringe 10, and thus the diluent is continuously sucked from the diluent container 11 into the second syringe 10. When the total amount of the diluent sucked into the second syringe 10 reaches a predetermined amount, the power unit 4 is stopped. It should be noted that the first sample buffer tube 8 preferably has enough length so as to prevent the measurement sample 7 stored in the sample buffer tube from entering into the second sample buffer tube 9 via this passage. Thus the measurement sample will be completely stored in the first sample buffer tube 8.

And then, the first switching unit 1 is switched into the constant-closed position, the second switching unit 2 and the third switching unit 3 are still in the respective constant-opened positions, so that the second syringe 10, the first syringe 5, the second sample buffer tube 9, the first sample buffer tube 8, the Lyse buffer tube 14 and the dispensing tube 16 are sequentially communicated to form a passage. And then, the power unit 4 is reversely driven so as to respectively push the pushing bars into the barrels of the first syringe 5 and the second syringe 10. And thus, the desired amount of the measurement sample stored in the sample buffer tube and a predetermined amount of the diluent sucked into the second syringe 10 are injected into the bath 15 via the passage. Consequently, the measurement sample with a special dilution ratio, i.e. the RBC/PLT count sample, is obtained. Finally, the power unit 4 is stopped.

Third step: cleaning the sample buffer tube and the Lyse buffer tube after the preparation of the RBC/PLT counting sample is completed:

The same procedures of substeps (2) and (3) of the first step can be performed in the third step, therefore the detail description for the third step is omitted here. After the sample buffer tube and the Lyse buffer tube 14 are cleaned, the power unit 4 is stopped.

Fourth step: preparing the measurement sample which is mixed with the Lyse and has a special dilution ratio, so as to obtain the WBC/HGB count sample:

(1) sucking a desired amount of the measurement sample and storing it into the sample buffer tube:

The first switching unit 1 and the second switching unit 2 are switched into the respective constant-closed positions, the third switching unit 3 is switched into the constant-opened position, so that the second syringe 10, the first syringe 5, the second sample buffer tube 9, the first sample buffer tube 8 and the aspirating tube 12 are sequentially communicated to form a passage. And then, the power unit 4 is driven so as to pull out the pushing bars of the first syringe 5 and the second syringe 10, and thus the measurement sample in the test tube 6 is sucked and stored into the sample buffer tube via the passage. When the measurement sample stored in the sample buffer tube reaches the desired amount, the power unit 4 is stopped. At this time, the measurement sample is stored into the first sample buffer tube 8 and the second sample buffer tube 9.

(2) sucking a predetermined amount of the diluent into the second syringe:

The first switching unit 1 and the second switching unit 2 are switched into the respective constant-opened positions, the third switching unit 3 is still in the constant-opened position, so that the second syringe 10 is communicated with the diluent container 11, while the first syringe 5, the second sample buffer tube 9, the first sample buffer tube 8, the Lyse buffer tube 14 and the dispensing tube 16 are sequentially communicated to form a passage. And then, the power unit 4 is driven so as to continuous to pull out the pushing bars of the first syringe 5 and the second syringe 10, and thus the diluent is sucked from the diluent container 11 into the second syringe 10. When the diluent sucked into the second syringe 10 reaches a predetermined amount, the power unit 4 is stopped. It should be noted that the second sample buffer tube 9 preferably has enough length so as to prevent the measurement sample 7 stored in the sample buffer tube from entering the first syringe 5 via this passage.

(3) sucking a prescribed amount of the Lyse and storing it into the Lyse buffer tube:

The first switching unit 1 is switched into the constant-closed position, the second switching unit 2 is still in the constant-opened position, and the third switching unit 3 is switched into the constant-closed position, so that the second syringe 10, the first syringe 5, the second sample buffer tube 9, the first sample buffer tube 8, the Lyse buffer tube 14 and the Lyse container 13 are sequentially communicated to form one passage. And then, the power unit 4 is driven so as to continuous to pull out the pushing bar of the first syringe 5 and the pushing bar of the second syringe 10, and thus the Lyse is sucked from the Lyse container 13 and stored into the Lyse buffer tube 14 via the passage. When the Lyse stored in the Lyse buffer tube 14 reaches a prescribed amount, the power unit 4 is stopped.

(4) preparing the measurement sample which is mixed with the Lyse and has a special dilution ratio, and thus obtaining the WBC/HGB count sample:

The first switching unit 1 is switched into the constant-closed position, the second switching unit 2 is still in constant-opened position, and the third switching unit 3 is switched into the constant-opened position, so that the second syringe 10, the first syringe 5, the second sample buffer tube 9, the first sample buffer tube 8, the Lyse buffer tube 14 and the dispensing tube 16 are sequentially communicated to form a passage. And then, the power unit 4 is reversely driven so as to respectively push the pushing bars into the barrels of the first syringe 5 and the second syringe 10. And thus, the desired amount of the measurement sample stored in the sample buffer tube, the prescribed amount of the Lyse stored in the Lyse buffer tube 14, and a predetermined amount of the diluent sucked into the second syringe 10 are injected into the bath 15 via the passage. Consequently, the measurement sample which is mixed with the Lyse and has a special dilution ratio is obtained, and thus the WBC/HGB count sample is obtained. Finally, the power unit 4 is stopped.

Fifth step, cleaning tubes after obtaining preparation the WBC/HGB count sample:

(1) The first switching unit 1 is switched into the constant-opened position, the second switching unit 2 and the third switching unit 3 are still in the respective constant-opened positions, so that the second syringe 10 is communicated with the diluent container 11. And then, the power unit 4 is driven so as to respectively pull out the pushing bars from the barrels of the first syringe 5 and the second syringe 10, and thus the diluent is sucked from the diluent container 11 into the second syringe 10. When the diluent sucked into the second syringe 10 reaches a predetermined amount, the power unit 4 is stopped.

(2) Then, the first switching unit 1 is switched into the constant-closed position, the second switching unit 2 and the third switching unit 3 are still in the respective constant-opened positions, so that the second syringe 10 is not communicated with the diluent container 11, but the second syringe 10, the first syringe 5, the second sample buffer tube 9, the first sample buffer tube 8, the Lyse buffer tube 14 and the dispensing tube 16 are sequentially communicated to form a passage. And then, the power unit 4 is reversely driven so as to respectively push the pushing bars into the barrels of the first syringe 5 and the second syringe 10. And thus, the predetermined amount of the diluent sucked into the second syringe 10 is injected into the bath 15 via the passage, and washes out the measurement sample, which is remained in the sample buffer tube and the dispensing tube 16, and the Lyse which is remained in the second sample buffer tube 9, the first sample buffer tube 8, the Lyse buffer tube 14 and the dispensing tube 16.

If necessary, the substeps (1) and (2) of the fifth step can be repeated several times so as to clean the Lyse buffer tube 14, the second sample buffer tube 9, the first sample buffer tube 8 and the dispensing tube 16, until the amount of the measurement sample and the Lyse which is remained in these pipes meets the desired requirement.

It should be noted that the fifth step during the above operation can be omitted. That is to say, the first step will be used to clean tubes during the repetition of the first step to the fourth step, therefore an additional step for cleaning tubes will not be required.

What is claimed is:

1. A device for distributing measurement sample and cleaning the measurement sample after analysis, the device comprising:

a diluent container;

an aspirating tube for retrieving a measurement sample;

a first syringe and a second syringe both of which are configured to be driven by a power unit for controlling a flow of the measurement sample, a lysing reagent, and the diluent according to a drive direction of the power unit;

a first switching unit configured to connect the first syringe to the second syringe or to connect the second syringe to the diluent container for controlling a flow of the measurement sample, the lysing reagent, or the diluent; and a second switching unit configured to connect the aspirating tube to a sample buffer tube or to connect the a dispensing tube to the sample buffer tube for controlling a flow of the measurement, the lysing reagent, or the diluent.

2. The device according to claim 1, wherein a reagent buffer tube, a reagent container for accommodating a reagent therein and a third switching unit are further provided between the sample buffer tube and the first syringe;

the reagent buffer tube is connected to the first syringe; and the third switching unit is configured to switch among connections which comprise connecting the reagent buffer port to the sample buffer tube and connecting the reagent buffer tube to the reagent container.

3. The device according to claim 1, wherein a reagent buffer tube, a reagent container for accommodating a reagent therein and a third switching unit are further provided between the second switching unit and the input port of the dispensing tube;

the reagent buffer tube is connected to the second switching unit; and the third switching unit is configured to switch among connections which comprise connecting the reagent buffer tube to the dispensing tube and connecting the reagent buffer tube to the reagent container.

4. The device according to claim 2, wherein the first switching unit, the second switching unit, and the third switching unit are solenoid valves.

5. The device according to claim 3, wherein the first switching unit, the second switching unit, and the third switching unit are solenoid valves.

6. The device according to claim 2, wherein the sample buffer tube comprises a first sample buffer tube and a second sample buffer tube which are connected in series, the first sample buffer tube is connected to the second switching unit, the second sample buffer tube is connected to the third switching unit, and an internal volume of the first sample buffer tube is smaller than an internal volume of the second sample buffer tube.

7. The device according to claim 3, wherein the sample buffer tube comprises a first sample buffer tube and a second sample buffer tube which are connected in series, the first sample buffer tube is connected to the second switching unit, the second sample buffer tube is connected to the first syringe, and an internal volume of the first sample buffer tube is smaller than an internal volume of the second sample buffer tube.

8. The device according to claim 1, wherein a pushing bar of the first syringe and a pushing bar of the second syringe are synchronously moved by the power unit.

9. The device according to claim 1, wherein a capacity of the first syringe is smaller than that of the second syringe, and the capacity of the second syringe is larger than that of the aspirating tube.

10. A device for distributing measurement sample and cleaning the measurement sample after analysis, the device comprising:
- a diluent container;
- an aspirating tube for retrieving a measurement sample;
- a first syringe and a second syringe both of which are configured to be driven by a power unit for controlling a flow of the measurement sample, a lysing reagent, and the diluent according to a drive direction of the power unit;
- a first switching unit configured to switch among connections which comprise connecting the first syringe to the second syringe and connecting the second syringe to the diluent container for controlling a flow of the measurement, the lysing reagent, or the diluent; and
- a second switching unit configured to switch among connections which comprise connecting the aspirating tube to a sample buffer tube and connecting a dispensing tube to the sample buffer tube for controlling a flow of the measurement, the lysing reagent, or the diluent, wherein
  - the device further comprises a reagent buffer tube, a reagent container for accommodating a reagent therein, and a third switching unit located between a sample buffer tube and the first syringe,
  - the reagent buffer tube is connected to a port of the first syringe,
  - the third switching unit is configured to switch among connections which comprise connecting the reagent buffer port to the sample buffer tube and connecting the reagent buffer tube to the reagent container, and
  - the sample buffer tube comprises a first sample buffer tube and a second sample buffer tube which are connected in series, wherein
    - the first sample buffer tube is connected to the second switching unit, the second sample buffer tube is connected to the third switching unit, and an internal volume of the first sample buffer tube is smaller than an internal volume of the second sample buffer tube.

11. A device for distributing measurement sample and cleaning the measurement sample after analysis, the device comprising:
- a diluent container;
- an aspirating tube for retrieving a measurement sample;
- a first syringe and a second syringe both of which are configured to be driven by a power unit for controlling a flow of the measurement sample, a lysing reagent, and the diluent according to a drive direction of the power unit;
- a first switching unit configured to switch among connections which comprise connecting the first syringe to the second syringe and connecting the second syringe to the diluent container for controlling a flow of the measurement, the lysing reagent, or the diluent; and
- a second switching unit configured to switch among connections which comprise connecting the aspirating tube to the sample buffer tube and connecting the dispensing tube to a sample buffer tube for controlling a flow of the measurement, the lysing reagent, or the diluent, wherein
  - the device further comprises a reagent buffer tube, a reagent container for accommodating a reagent therein, and a third switching unit located between the second switching unit and the dispensing tube,
  - the reagent buffer tube is connected to the second switching unit;
  - the third switching unit is configured to switch among connections which comprise connecting the reagent buffer tube to the dispensing tube and connecting the reagent buffer tube to the reagent container, and
  - the sample buffer tube comprises a first sample buffer tube and a second sample buffer tube which are connected in series, wherein the first sample buffer tube is connected to the second switching unit, the second sample buffer tube is connected to the first syringe, and an internal volume of the first sample buffer tube is smaller than an internal volume of the second sample buffer tube.

\* \* \* \* \*